United States Patent
Goertler et al.

(10) Patent No.: US 10,515,316 B2
(45) Date of Patent: Dec. 24, 2019

(54) SYSTEM AND METHOD FOR USING DATA OBTAINED FROM A GROUP OF GEOGRAPHICALLY DISPERSED MAGNETIC RESONANCE SYSTEMS TO OPTIMIZE CUSTOMER-SPECIFIC CLINICAL, OPERATIONAL AND/OR FINANCIAL PERFORMANCE

(71) Applicant: SIEMENS HEALTHCARE GMBH, Erlangen (DE)

(72) Inventors: Georg Goertler, Baiersdorf (DE); Sultan Haider, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 779 days.

(21) Appl. No.: 15/089,060

(22) Filed: Apr. 1, 2016

(65) Prior Publication Data
US 2017/0286611 A1 Oct. 5, 2017

(51) Int. Cl.
*G06N 20/00* (2019.01)
*G06F 19/00* (2018.01)
*G16H 50/20* (2018.01)

(52) U.S. Cl.
CPC ............ *G06N 20/00* (2019.01); *G06F 19/00* (2013.01); *G06F 19/321* (2013.01); *G16H 50/20* (2018.01)

(58) Field of Classification Search
CPC ...... G06N 99/005; G16H 50/20; G06F 19/00; G06F 19/321
See application file for complete search history.

(56) References Cited

U.S. PATENT DOCUMENTS

| | | | |
|---|---|---|---|
| 6,885,884 B2 | 4/2005 | Goertler | |
| 8,595,553 B2 | 11/2013 | Goertler et al. | |
| 2003/0215125 A1* | 11/2003 | Yokoi | G16H 40/40 382/131 |
| 2011/0302461 A1* | 12/2011 | Goertler | G16H 40/40 714/57 |
| 2013/0030641 A1* | 1/2013 | Olsen, III et al. | G05B 23/0283 701/31.6 |
| 2013/0311472 A1* | 11/2013 | Cohen-Solal | G06F 19/321 707/737 |
| 2013/0315475 A1* | 11/2013 | Song | G06K 9/00369 382/154 |
| 2017/0235899 A1* | 8/2017 | Othman | G06F 19/328 705/2 |

OTHER PUBLICATIONS

Barry Wllks, Basic Computer Design, as archived Mar. 3, 2001, http://spike.scu.edu.au/~barry/dp234/dp234-t1.html (Year: 2001).*

* cited by examiner

*Primary Examiner* — Austin Hicks
(74) *Attorney, Agent, or Firm* — Laurence Greenberg; Werner Stemer; Ralph Locher

(57) ABSTRACT

A system and method for optimizing customer magnetic resonance systems is provided. An automation system gathers data from a geographically dispersed network of installed magnetic resonance systems, which data is mined and analyzed in order to recognize patterns about the best practices of the installed base. Customer-specific variables for customer magnetic resonance systems are then optimized, based on the recognized patterns. More particularly, customer specific protocols and hardware/software configurations can be calculated and optimized, by making use of data mined from best-in-class customers having similar profiles.

18 Claims, 6 Drawing Sheets

SYSTEM AND METHOD FOR USING DATA OBTAINED FROM A GROUP OF GEOGRAPHICALLY DISPERSED MAGNETIC RESONANCE SYSTEMS TO OPTIMIZE CUSTOMER-SPECIFIC CLINICAL, OPERATIONAL AND/OR FINANCIAL PERFORMANCE

REFERENCE TO A COMPUTER PROGRAM LISTING APPENDIX

A computer program listing appendix is being submitted on two compact discs (an original and a duplicate), by Express Mail under 37 CFR § 1.10, and electronically herewith. The computer program listing appendix is incorporated by reference herein. Each of the compact discs is in IBM-PC Machine Format and is compatible with MS-Windows and contains the computer program listing appendix consisting of the following two files: "XProtocol.txt", created on Apr. 1, 2016 and having a file size of 86,781 bytes; and "Protocol_log_file.txt", created on Apr. 1, 2016 and having a file size of 12,134 bytes.

BACKGROUND OF THE INVENTION

Field of the Invention

The present invention relates to a system and method for optimizing magnetic resonance systems, and more particularly to a system and method for observing a network of installed magnetic resonance systems to analyze patterns and, based on recognized patterns, to optimize customer specific variables for customer magnetic resonance systems.

Description of the Related Art

Purchasers of magnetic resonance (MR) systems, especially new ones, often lack experience on handling MR systems. The Magnetom Aera and Skyra magnetic resonance imaging (MRI) scanners by Siemens Healthcare, for example, offer over 3000 available MRI protocols (i.e., combinations of various MRI sequences designed to optimally assess a particular region of the body and/or pathological process). Every protocol for an MR system additionally includes a number of parameter combinations that have to be adjusted by the user for the best results (i.e., for image quality, measurement time requirements, etc.). Often, different MR customer sites perform differently, even if they use the same software and hardware components. This is due, in part, to customer behaviors that include usage of the MR system, customer defined protocols, adjustment of the parameters, infrastructural settings (e.g., cooling), etc.

Currently, customer training is used to address a lack of experience with MR equipment. However, such customer training is expensive. Additionally, application specialists can help customers find a customer-specific protocol tree. Particular user protocols can then be selected from a "User Protocol Tree" that is typically stored in, and accessed through, an MR scanner.

MR systems at geographically dispersed locations can be observed remotely, and data mining techniques can be used to establish error patterns for tracked MR devices. See, for example, U.S. Pat. No. 8,595,553 to Görtler et al. (the "'553 Görtler patent"), that reference being incorporated herein, by reference. Additionally, U.S. Pat. No. 6,885,884 to Görtler (the "'884 Görtler patent"), incorporated herein by reference, discloses a method for simulating the use of a system option for a technical apparatus, in which data from technical apparatuses that relate to the configuration and/or the usage of the apparatuses are collected and stored in a central data bank, and relationships between collected, stored data and/or between collected, stored and additionally prescribable data are produced. In the '884 patent, a system option for a technical apparatus is simulated based on the data placed in relationship to one another.

Additionally, Siemens Healthcare has developed an automation platform to observe, and obtain data from, installed Siemens MR systems, worldwide and perform hardware monitoring, data mining and pattern learning. The data mined by the automation platform can be used to analyze patterns and evaluate stability metrics. Further, as discussed in the '553 Görtler patent, an automated learning process can be used to analyze data for globally dispersed locations to provide reactive and/or predictive/preventive service.

Using the Siemens Healthcare automation platform it can be easily observed that customers do not use all of the 3000+ available protocols available in products such as the Magnetom Aera and Skyra magnetic resonance imaging (MRI) scanners by Siemens Healthcare, and that customers often change the names and parameters of the protocols they do use. This means that a lot of money is wasted in development, testing and validation costs for MR systems. Additionally, the customer then needs to pay for application support. However, in spite of support from application specialists, it is difficult to find the right adjustment of the protocols with respect to a particular customer's portfolio.

What is needed is a system and method for evaluating data mined from a large number of geographically dispersed MR system customer sites to find best-in-class customers and determine the parameters, hardware and software components they use. What is further needed is a system and method that can determine the best practices from among all of the geographically dispersed MR system customer sites and use them to formulate optimized customer-specific protocols.

BRIEF SUMMARY OF THE INVENTION

The present invention is particularly suited to overcome those problems which remain in the art in a manner not previously known or contemplated. It is accordingly an object of the invention to provide a system and method that evaluates data mined from a large number of geographically dispersed MR system customer sites to find best-in-class customers and determine the parameters, hardware and software components they use, in order to formulate optimized customer protocols.

Although the invention is illustrated and described herein as embodied in a system and method for using data obtained from a group of geographically dispersed magnetic resonance systems to optimize customer-specific clinical, operational and/or financial performance, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

The foregoing background, as well as the following detailed description of the preferred embodiments, is better understood when read in conjunction with the appended drawings. For the purpose of illustrating the invention, there is shown in the drawings an exemplary embodiment that is presently preferred, it being understood however, that the invention is not limited to the specific methods and instrumentality's disclosed. Additionally, like reference numerals represent like items throughout the drawings. In the drawings.

DETAILED DESCRIPTION OF THE INVENTION

Before explaining the disclosed embodiment of the present invention in detail, it is to be understood that the invention is not limited in its application only to the details of the particular arrangement shown since the invention is capable of other embodiments. Also, the terminology used herein is for the purpose of description and not of limitation. For the present application, the term "magnetic resonance" has been abbreviated "MR". Magnetic resonance imaging has been abbreviated "MRI". "Cardovascular magnetic resonance has been abbreviated "CVMR" or just "CMR". The term "XMART" will be used herein to describe an automation platform developed by Siemens Healthcare to observe, and obtain data from, installed Siemens MR systems, worldwide. "Best-in-class" and "best practices" refer to a high current performance level in an industry, which is used as a standard or benchmark to be equaled or exceeded. "User protocols", "customer protocols" or just "protocols", as used herein, are combinations of various MRI sequences designed to optimally assess a particular region of the body and/or pathological process that are selectable by the user, usually from a user protocol tree, for execution by an MR device. The terms "MR system", "MR device" and "MR apparatus", both in the singular and in the plural, are used interchangeably, herein. Additionally, reference to a computer, herein, should be understood to encompass, without limitation, one or more computers or servers configured to perform the recited functions, whether local to one another (i.e., a centralized computer system) or distributed (i.e., a de-centralized, peer-to-peer or networked), and/or whether in the possession or control of a service provider (as used herein), or third-party computers or data centers (e.g. cloud computing).

Figure 1:
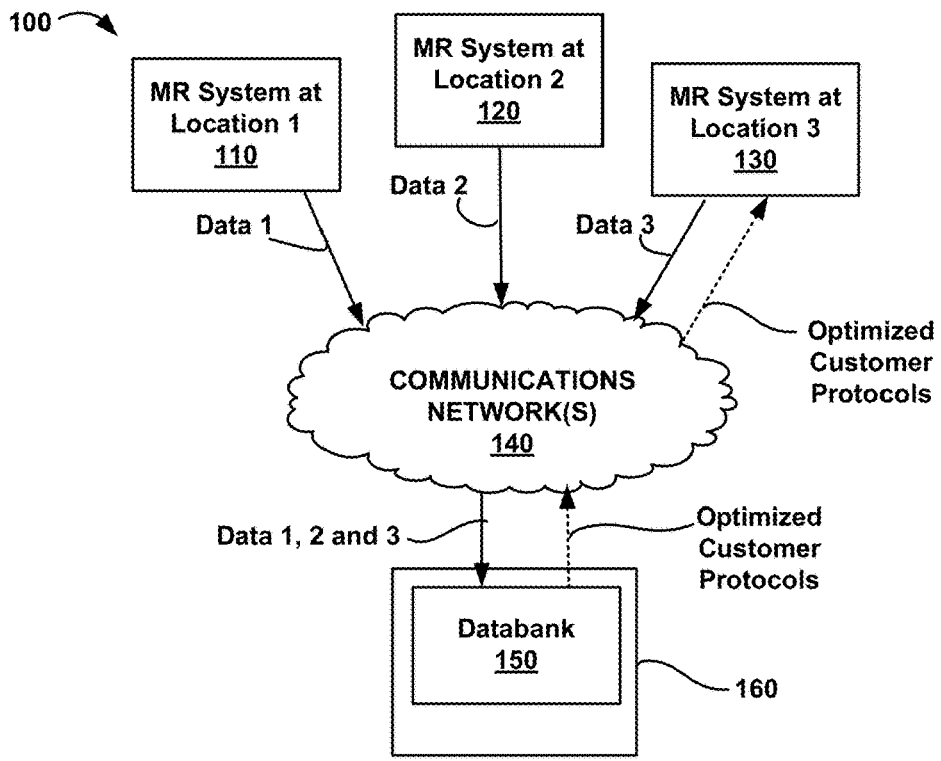
FIG. 1 is a simplified block diagram of a system in accordance with one particular embodiment of the invention.

Referring now to FIG. 1, there is illustrated an exemplary system 100 according to one particular embodiment of the invention. The system 100 gathers data from thousands of geographically dispersed MR customer sites to identify best-in-class customers and the protocols, parameters, hardware and software that they use to make patient measurements using a MR device. Note that, FIG. 1 is a simplified illustration showing MR systems at only three locations. However, this is purely illustrative and not meant to be limiting, as it should be understood that a large network of MR systems installed at geographically dispersed locations will be present, in use.

According to the present invention data regarding the particular MR system operations performed by each MR system customer 110, 120, 130 is provided from equipment at the location to one or more non-transitory memory devices configured as databases or "databanks" 150 of, or accessible by, a computer (usually a server) of the service provider 160, via an interface to a communication network or networks 140. In one particular embodiment, data 1, data 2 and data 3 are gathered by an automation tool, for example, using a system as described in the '884 Görtler patent, incorporated herein by reference. Data gathered can be analyzed by a server or other computing device associated with the service provider 160 and having access to the one or more databanks 150. Service provider 160 is, in the preferred embodiment, geographically remote from the geographically dispersed MR systems at Locations 1, 2 and 3.

More particularly, in the embodiment illustrated in FIG. 1, data 1, data 2 and data 3 are collected in automated fashion from one or more technical apparatuses at locations 1, 2 and 3, respectively, and stored in the databank 150 accessible by the remote service provider 160. If desired, the collected data can be filtered, so that only specific types of data are forwarded to the one or more databanks 150. An overloading of the databank(s) with relatively irrelevant data can thus be avoided. The service provider 160, using a computer, can then analyze the data in order to identify best-in-class customer systems and, based on this identification, can provide other customer systems with customer-specific protocols, offers and other information. Although a single databank 150 is illustrated as being at the location of the service provider 160, this is not meant to be limiting, as databank 150 can be made up of one or more databanks at distributed locations which are accessible by the service provider 160 via a communications network.

Additionally, the automated collection of data is performed over one or more communication networks 140 which can be, but is not limited only thereto, one or more of the Internet, an Intranet, an Extranet and/or a public or private telecommunication system. In one particularly preferred embodiment, the apparatuses from which data is to be collected at each location 1, 2 and 3 are constantly connected to the one or more communication networks 140 and communicate data 1, data 2 and data 3 to the one or more databank 150 on their own, or on demand. Alternately, the apparatuses can be periodically connected to one or more communication networks 140 in order to provide collected batches of data to one or more databanks 150 for processing.

The data 1, 2, 3 collected in the one or more databanks 140 includes, in the exemplary embodiment, configuration data for the MR apparatuses at Locations 1, 2 and 3, including data characterizing the hardware and software equipment of the MR system devices at locations 1, 2 and 3. For example, the configuration data can include, among other things, information about which cons are installed in the magnetic resonance apparatus and with which software components, particularly measurement programs, the magnetic resonance apparatus is equipped. Further, data over the usage of the devices of the MR systems at each location 1, 2 and 3 are collected, particularly data about when, how long and for which examinations or treatments hardware or software components of the devices are used by the customer. In one particular exemplary embodiment, this data includes information, about when various measurements have been carried out, as to which coil was used for which examination, and which protocols or measurement sequences were used. Other workflow data for the devices can additionally be collected, for example, data providing information about the types of patient examinations (e.g., heart examinations), their frequency, and their time duration.

The gathered data is mined for data for the best practices of the installed MR system base, using a computer associated with the service provider. In one particular embodiment of the invention, the data was automatically processed, analyzed and displayed using a data mining tool known as RapidMiner, which is an open-source development project available for downloading from the Internet that supports various data mining algorithms and visualization methods for both input and output data. Other comparable data mining tools are commercially available.

Figure 2:
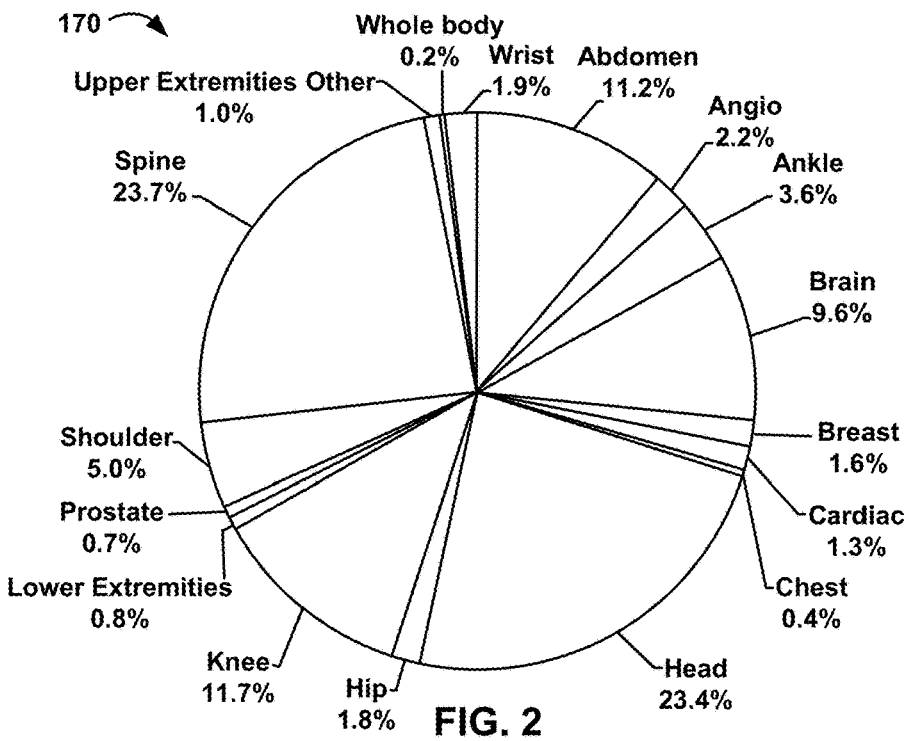
FIG. 2 illustrates an exemplary graphic that can be provided from data obtained according to one particular embodiment of the invention.
Figure 3:
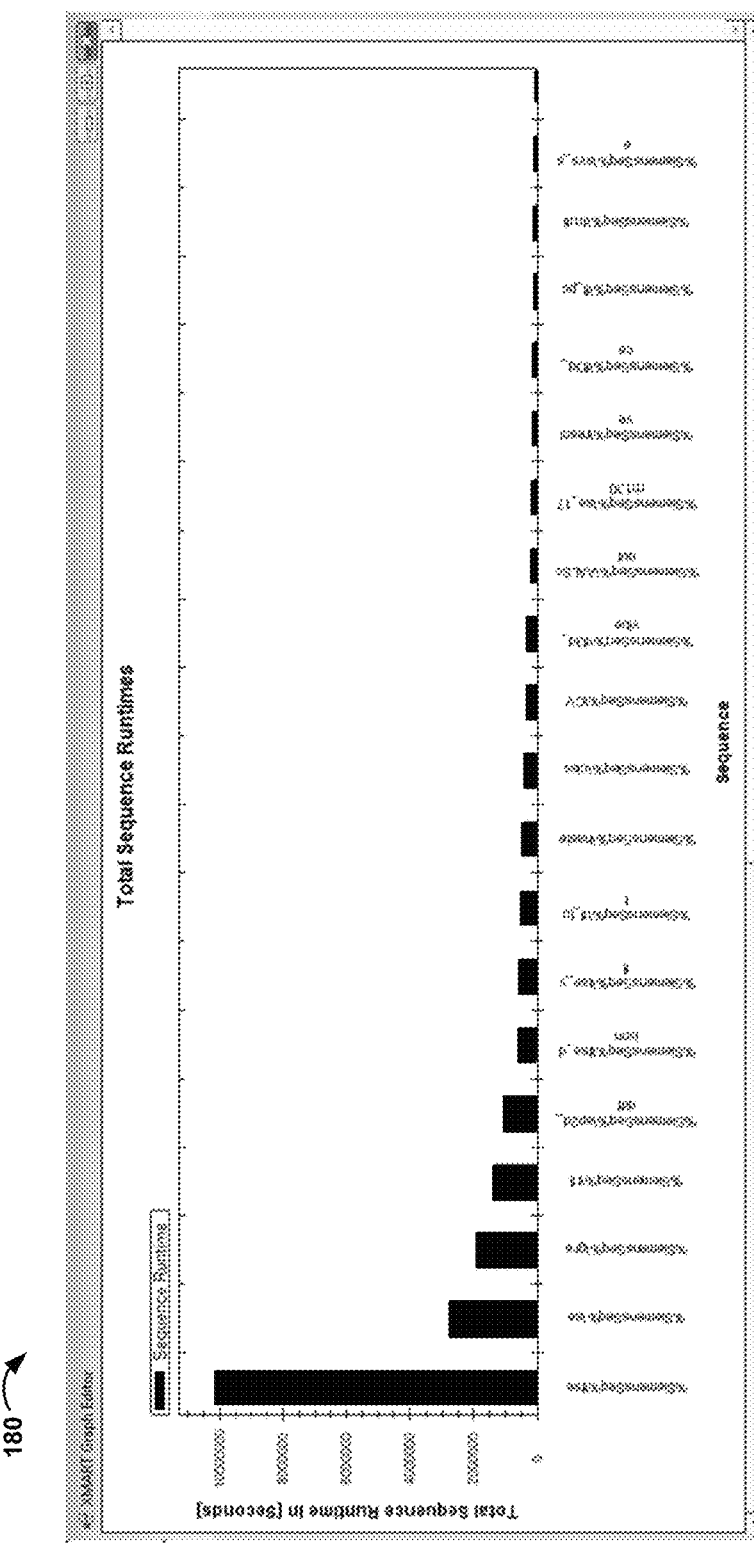
FIG. 3 shows an exemplary bar graph illustrating the sequence usage for an MR system of a single customer, according to one particular embodiment of the invention.

More particularly, the data 1, 2, 3 undergoes statistical analysis. Results of the statistical analysis can then be formatted, as desired. For example, referring now to FIGS. 1 and 2, there is shown one particular example 170 of a customer-specific report that can be generated from data captured from the system 100. In one particular embodiment, data from one of the geographically dispersed MR system customers 110, 120 or 130 is analyzed to provide, in this case, a pie chart illustrating the different body parts, by percentage, examined over a predefined time period by that particular MR system customer 110, 120 or 130. Similarly, FIG. 3 shows an exemplary bar graph 180 illustrating the sequence usage for the MR system of a single customer 110, 120 or 130, derived from analyzing the data obtained from that particular user system 110, 120 or 130 of FIG. 1.

By analyzing the data collected, a service provider 160 can derive customer-specific usage of the MR apparatuses and identify the protocols used and measurements taken by best-in-class customers. The best-in-class protocols and measurements so identified can be used by the service provider 160 to optimize the use of the MR equipment of other, similarly equipped customers.

For example, the data received from the MR system customers 110, 120, 130 can be used to optimize the protocols in the MR system customers 110, 120, 130, addressing customer-specific factors. Customer protocols optimized in this way offer higher performance and standardized workflows. Additionally, the data 1, 2, 3 can be analyzed in order to provide specific customers 110, 120 and/or 130 with offers that could help optimize the customer's use of the MR system including, but not limited to, offers for different applications, coils, trainings, etc., based on their determined system features.

Figure 4:
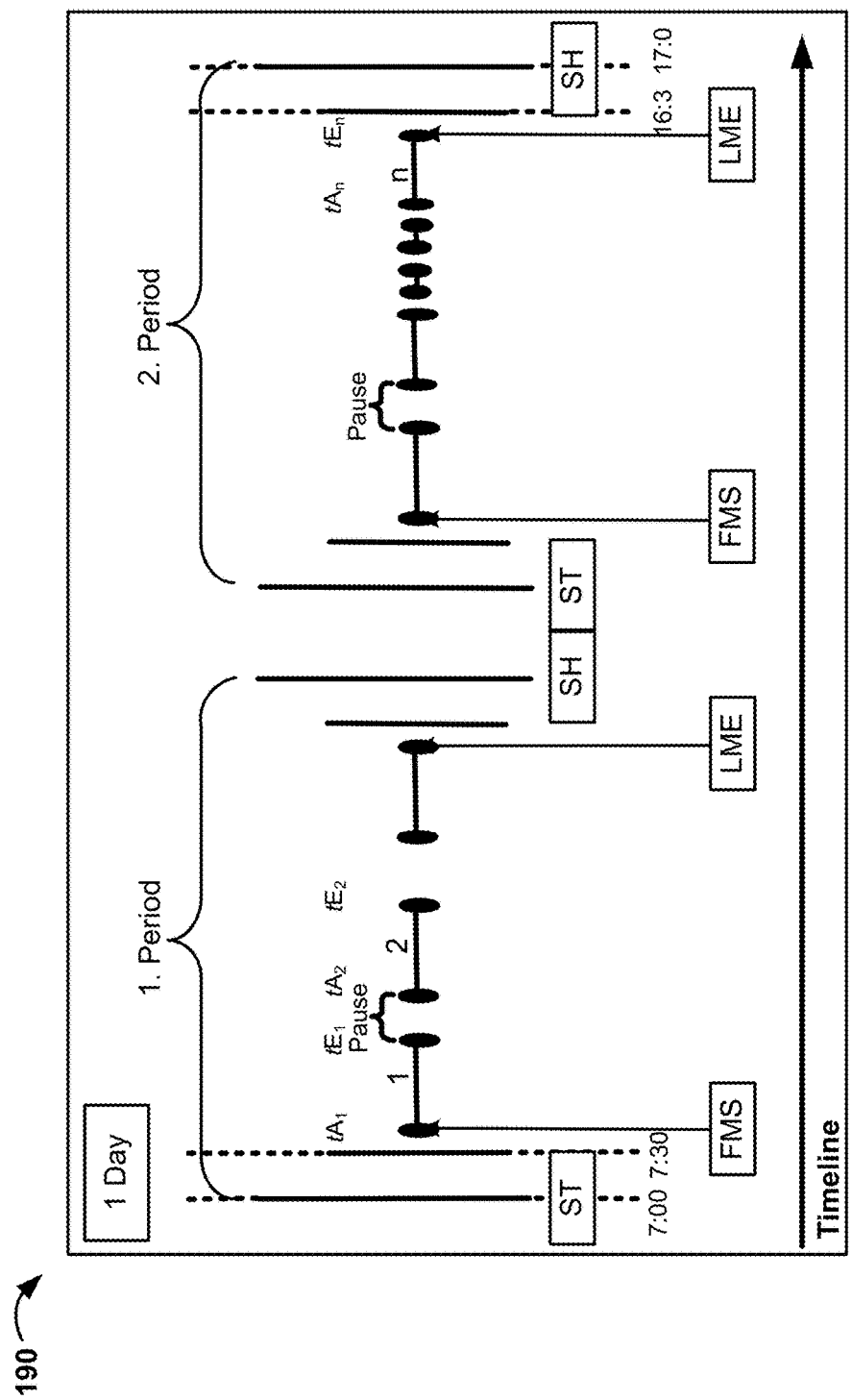
FIG. 4 illustrates an exemplary graphic that can be provided from data obtained according to one particular embodiment of the invention.

In one particular embodiment of the invention, optimization is calculated by determining: (a) various parameters such as repetition time (TR), echo time (TE), field of view (FOV), number of slices, flip angle, etc.; (b) the measurement time and idle time; (c) the type of sequences; (d) various body parts examined; (e) hardware components used, e.g., types of coils, patient tables, etc.; (f) software components and license portfolio; (g) usage of contrast agent; and (h) information about various location of the MR systems. For example, referring now to FIG. 4, there is illustrated a FIG. 190 showing single periods being watched in order to determine measurement performance (i.e., examination time, idle time, etc.) with respect to different customer behaviors. The data obtained is then subjected to data mining and statistical analysis, clustering of customers and learning decision trees in order to create customer-specific, optimized protocols.

Figure 7:
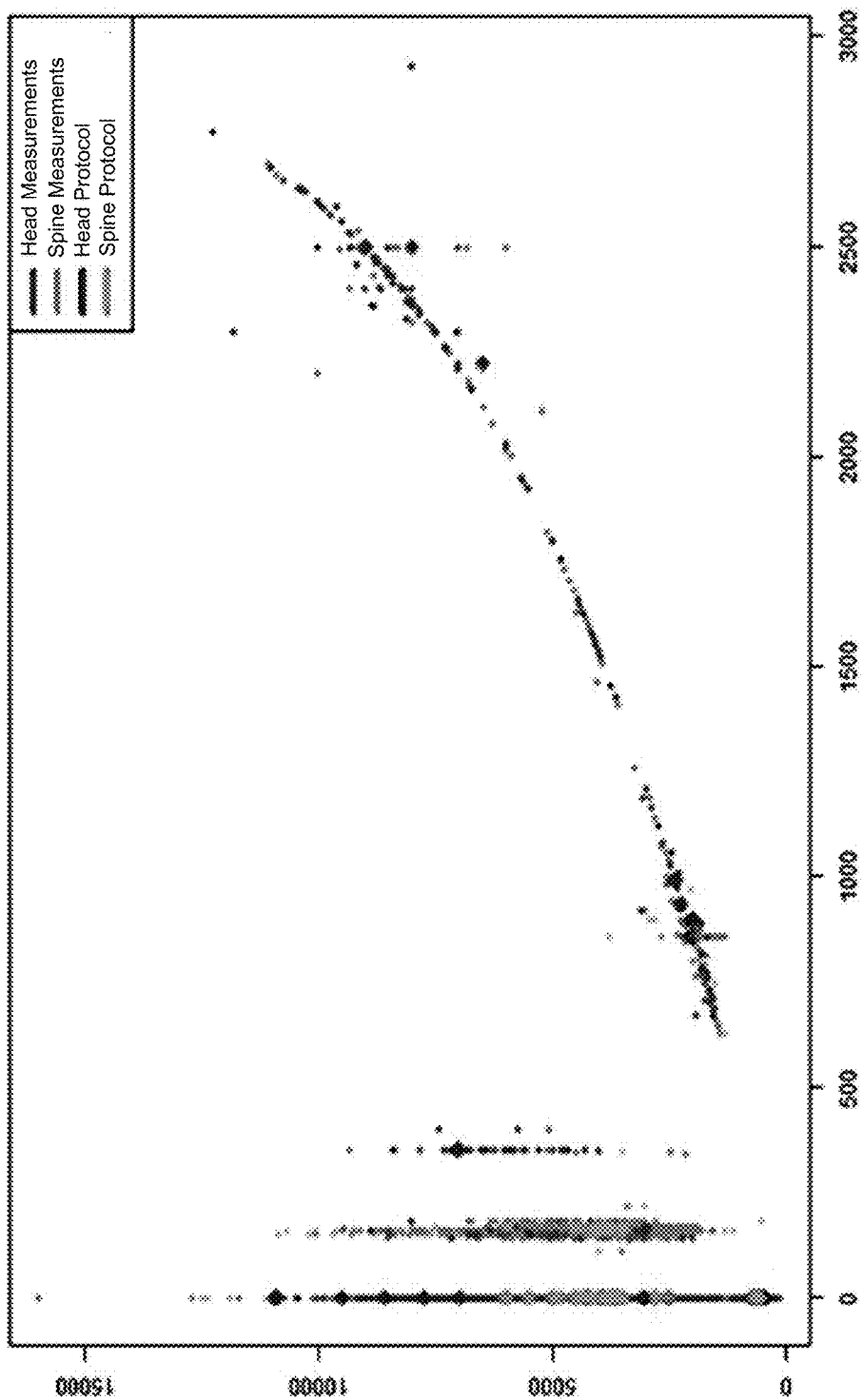
FIG. 7 is an exemplary chart illustrating implementation of provided MR system protocol parameters and customer measurements for head and spine body regions.

By identifying best-in-class protocols with respect to body parts, type of customers and portfolio, the collected data can be used to derive best practices optimizations that can be provided to customers to optimize their specific systems according to the successes of other similarly situated customers. For example, a service provider 160 can utilize patterns found as a result of the data mining and statistical analysis to provide optimized protocols to customers, thus reducing the learning curve and training time for customers. FIG. 7 illustrates one example in which the service provider 160 delivers, based on analyzed data, optimized MR system protocol parameters used by a customer to obtain optimized MR measurements for the head and spine body regions.

Referring now to FIGS. 1 and 4-6, there will now be described an exemplary data mining model in accordance with one particular embodiment of the invention. More particularly, an MR system customer 110 at location 1 utilizes certain MR operation sequences during operation in a day. The data (data 1) regarding the use of the MR system apparatuses, including the protocols used by the MR apparatus, are provided to the service provider 160 via one or more communications networks 140. The data for each MR system in the geographically dispersed network of MR systems is thus collected and stored in one or more databanks 150. The data for each customer is filtered and analyzed.

For example, as discussed above, FIG. 3 illustrates the total sequence runtime (in seconds) of each sequence used by a customer when operating their MR apparatuses during a particular time period. In one particular embodiment of the invention, the service provider will utilize the information to find best-in-class customer operations and to identify customers that can benefit from receiving optimized configuration data and protocols modeled after the best-in-class customer systems identified. In the present embodiment, a model is configured, using the data mining software, to import, process, analyze and visualize the data for each customer and for groups of customers, as desired.

Figure 5:
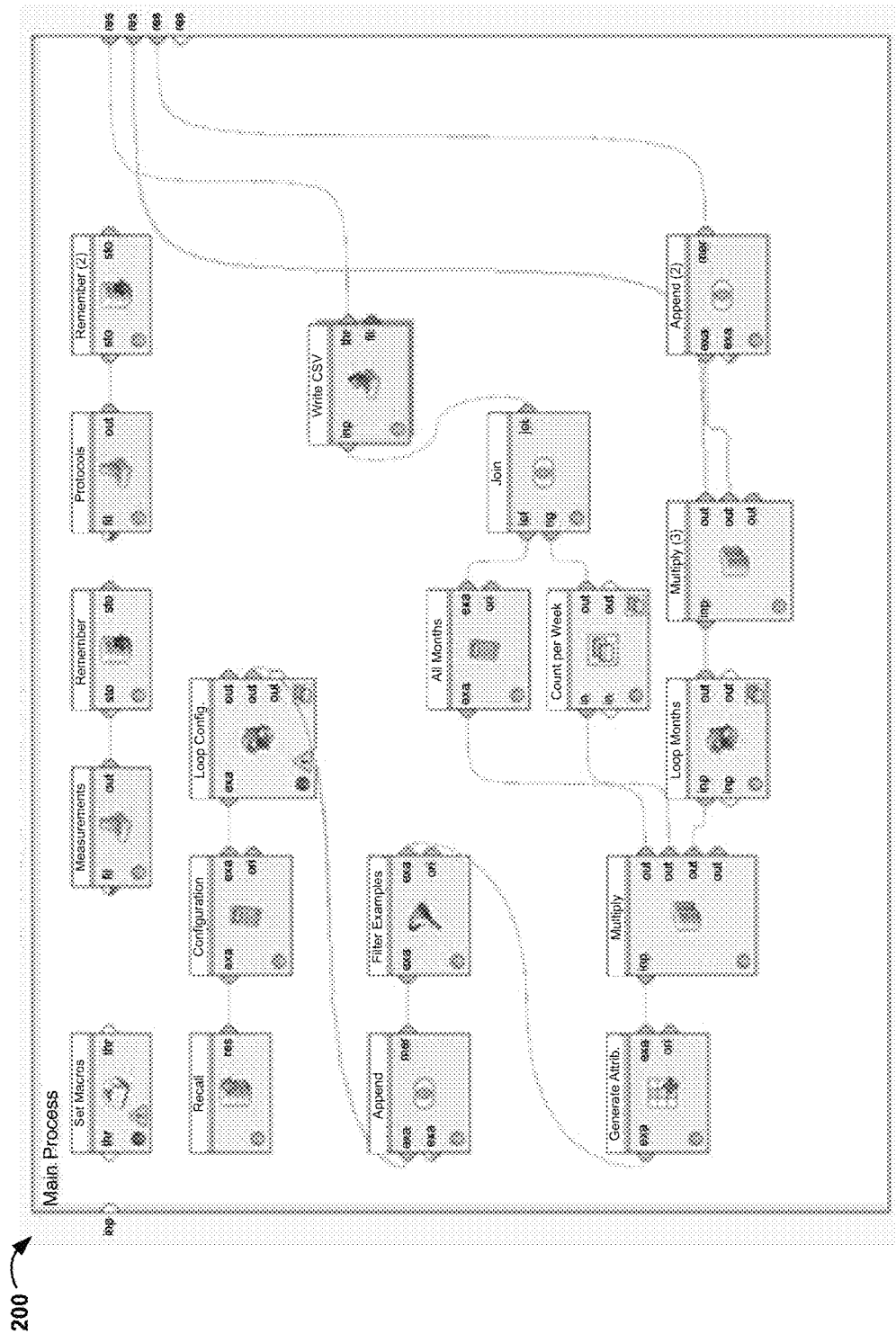
FIG. 5 is an exemplary data mining model in accordance with one particular embodiment of the invention.

In the present embodiment, a training model is created by the service provider 160 to analyze the data that, in the present example, is used to determine customer clustering based on sequence parameter usage for similarly situated customers (i.e., having similar hardware or software or usages, etc.). FIG. 3 illustrates a graphical representation of sequence usage data collected from a particular time period for a single customer. The data obtained from the customer is imported from the data bank 150 to the data mining program, which processes the data. FIG. 5 illustrates an exemplary data mining model 200 used to calculate the distance of sequence parameters for a customer. The process illustrated is set up in this example using the RapidMiner data mining tool (and in particular, RapidMiner Studio), but other data mining programs and tools can be used without limiting the scope and spirit of the present invention.

More particularly, software (stored in non-transitory memory of a computer or server and executed by a processor of that computer or server) is used by the service provider to build a process (analytics workflow) that will find predictive relationships that can be described with a model. The model 200 can then be applied to all data to analyze the practices of each customer, relative to a group of customers. As discussed above, the type of data obtained from each customer can include, but is not limited to: information about which coils are installed in the magnetic resonance apparatus and with which software components, particularly measurement programs, the magnetic resonance apparatus is equipped; data about when, how long and for which examinations or treatments hardware or software components of the devices are used by the customer; information about when various measurements have been carried out, as to which coil was used for which examination, and which protocols or measurement sequences were used; and/or other workflow data for the devices, such as, data providing information about the types of patient examinations (e.g., heart examinations), their frequency, and their time duration.

The workflow of the exemplary model "Main Process" 200, illustrated in FIG. 5, will now be described, in brief. The Main Process 200 is one particular example of a data mining model executed by a processor affiliated with the service provider and used to calculate the distance of sequence parameters between customers for use in later customer clustering and pattern recognition analysis. First, in the model 200, a "Set Macros" operator is used to define multiple macros which can be used in parameter values of succeeding operators in the "Main Process" 200. The measurements and protocols data obtained from the network of MR systems via a communications network, must be analyzed to evaluate each customer with respect to other, similarly situated customers. To this end, a read operator ("Measurements") retrieves a file containing measurement data obtained from the network of customer MR devices, which data is then stored in the object store of the process by a "Remember" operator. Similarly, a read operator ("Protocols") retrieves a file containing data on the protocols used by the customers, which data is also stored in the object store of the process 200 by the "Remember (2)" operator.

A "Recall" operator can be used to retrieve the measurements and protocols stored in the Remember and Remember (2) operations, and/or other configurations and/or usage data collected from the network of customer MR devices and stored in the data store. In the example shown, customer "Configuration" data is recalled from the data store and aggregated to create an example set showing the results of selected aggregation functions (typically know from SQL) selected by the service provider. A loop operator is then performed, wherein a subprocess is iteratively executed for all examples of the aggregated example set of configuration data. An "Append" operation is then performed to build a merged example set from two or more compatible example sets by adding all examples into a combined set and the combined example set is then filtered (i.e., "Filter Examples" operator). The combined and filtered set is subjected to a "Generate Attributes" operator, which constructs new, user defined attributes using mathematical expressions and provides, at its output, the example set having the new attributes, which is received at the input of a "Multiply" operator which copies its input set to all connected output ports without modification.

Thus, the example set having new attributes is provided to: an Aggregation operator ("All Months") that aggregates the example set for all months; to a subprocess operator ("Count per week"); and to a loop operator ("Loop Months"). The output sets from the aggregation and subprocess operators are joined ("Join") and written to a Comma-Separated Values (CSV) file ("Write CSV"). The output of the loop operator ("Loop Months") is provided to a multiply operator ("Multiply 3") from which it is provided as a process result, as well as, provided to an append operator ("Append (2)") to create a merged example set, which is additionally provided as a result of the process.

Figure 6:
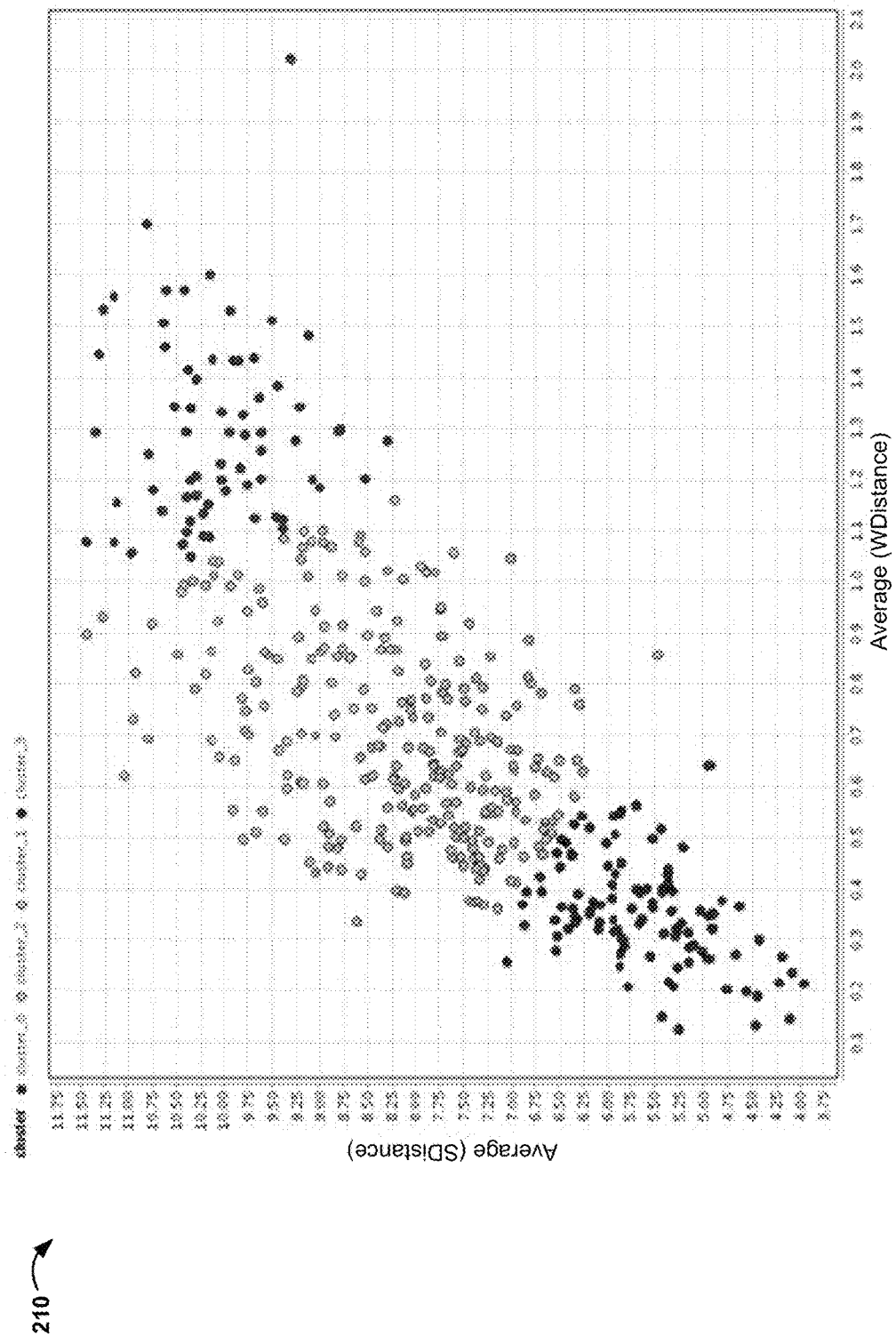
FIG. 6 is an exemplary graph illustrating customer clustering due to sequence parameters usage of the customers.

In operation, the distance of sequence parameters calculated in the data model of FIG. 5 are used to cluster the customers relative to one another. Referring now to FIG. 6, in one particular embodiment of the invention, customers are clustered by obtaining, for every customer measurement, the two nearest neighbors: one for WDistance and one for SDistance. Given a customer, the average WDistance with respect to the average SDistance is looked at for all measurements of this customer. Each point on the graph 210 represents one customer. In the lower left corner are those customers that do their measurements similar to the service provider's protocols (in this case—Siemens). In the upper right corner are those customers who use different protocols. The customers are clustered, in this case, based on their position relative to their protocols usage. In the present example, customers exhibiting sequence usage in the upper right of the graph 210 can be optimized by conforming their sequence usage with similarly situated customers clustered at the other end (i.e., bottom left) of the graph 210. Note that, although in the exemplary graph 210 customers were clustered on the basis of their sequence parameter usage, the invention is not meant to be limited thereto, as clustering can be performed according to other criteria, in order to identify optimal customer MR systems and similarly situated customer MR systems that could be optimized using configuration, usage and/or protocol information derived from the optimal customer MR systems.

Once the customer MR systems have been clustered, as described, learning of user protocol/decision trees of MR systems identified as exemplary can be used as the basis for creating customer-specific, optimized protocols for other members of the cluster. For example, referring back to FIG. 6, outlying customer MR systems can be identified and provided with information on the protocols and measurements used by similarly situated best-in-class customer MR systems, also identified from the cluster data.

In summary, the clustered data can be used to identify best-in-class customers, their system configurations, protocols and usage practices, as well as customers that could use help in optimizing their systems and/or usage. Referring back to FIG. 1, the data collected and analyzed by the service provider 160 can be used to provide new products and/or contracted services/service modules to customers 110, 120 and/or 130.

Financial Module:

For example, the service provider 160 can use the analysis performed to provide the customers 110, 120 and/or 130 with a financial module in which the service provider calculates, reports and/or optimizes the customers return on investment for the equipment utilized. Additionally, the analyzed data can be used to provide customer specific offers for applications, coils, trainings, etc., as determined by the clients usage of the equipment and protocols, as illustrated by the client clustering and other data. The analyzed data can additionally be used to provide customers with actual performance information such as, but not limited to, scanner performance, electricity usage, cooling system usage, status of the components, and proactive service. Additionally, by analyzing the data and clustering similarly situated clients, the best practices of similarly equipped customers could be determined and provided to other customers in order to optimize the system configurations and operations of the other customers.

Operational Module:

Additionally, the analyzed data can by the service provider 160 to perform fleet management for the customers.

Clinical Module:

Analyzed data and clustering of customers based on their measurements taken and protocols used can help identify customers having best-in-class protocols for that specific customer's portfolio, e.g., specific to that customer's usage/examinations. Best-in-class protocols so identified can be marketed by the service provider to other clients in order to achieve image quality improvements for those clients. In particular, protocols learned from customers identified as best-in-class by the clustering can be programmed into the MR systems of other, similarly situated customers not already using those protocols, in order to optimize a remote customer's MR system. In one particular embodiment, the customer's MR system is programmed with the learned protocols electronically, via the communications network.

As can be seen from the foregoing description, optimized customer specific protocols can be calculated and hardware/software configurations evaluated by making use of data mined from best-in-class customers having similar profiles.

While the invention has been described, disclosed, illustrated and shown in various terms of certain embodiments or modifications, which it has presumed in practice, the scope of the invention is not intended to be, nor should it be deemed to be, limited thereby and such other modifications or embodiments as may be suggested by the teachings herein are particularly reserved, especially as they fall within the breadth and scope of the claims here appended. Accordingly, while a preferred embodiment of the present invention is shown and described herein, it will be understood that the invention may be embodied otherwise than as herein specifically illustrated or described, and that within the embodiments certain changes in the detail and construction, as well as the arrangement of the parts, may be made without departing from the principles of the present invention as defined by the appended claims.

The invention claimed is:

1. A method for optimizing a customer magnetic resonance (MR) system, comprising the steps of:
    receiving data from a network of geographically dispersed customer MR systems at a computer geographically remote from the customer MR systems, the data including configuration data for a plurality of geographically dispersed customer MR systems, including data characterizing the hardware and software equipment of the MR system devices of the customer MR systems;
    storing the received data in a non-transitory memory device accessible by the computer;
    performing, with the computer, data mining of the data and analyzing the mined data to perform a clustering of customer MR systems in order to identify customer-specific usage of the MR systems and at least one protocol used by at least one of the geographically dispersed customer MR systems, wherein the computer is configured to cluster a plurality of customer MR systems by:
        for every measurement obtained from a customer MR system of the plurality, finding two nearest neighbors, and obtaining a first distance for a first nearest neighbor and obtaining a second distance for a second nearest neighbor;
        finding an average first distance with respect to an average second distance for all measurements of the customer MR system; and
        clustering the plurality of customer MR systems based on a position of each customer MR system for the average first distance and the average second distance; and
    providing information based on the at least one protocol learned to another customer MR system based on the clustering, said providing including electronically programming the another customer MR system with the said at least one protocol learned in order to optimize the another customer MR system.

2. The method of claim 1, wherein the at least one protocol includes at least one best-in-class protocol for operating the customer MR system.

3. The method of claim 2, wherein the information provided includes a protocol derived from the at least one best-in-class protocol.

4. The method of claim 3, wherein the information provided further includes at least one measurement for at least one particular body region.

5. The method of claim 1, wherein the received data includes MR system sequence usage for at least one customer.

6. The method of claim 1, wherein clustering is performed using all measurements for at least one customer.

7. The method of claim 1, wherein the information provided includes at least one protocol learned from the customer MR system and provided to the another customer MR system.

8. The method of claim 7, wherein the at least one protocol learned is provided to the another customer MR system electronically via a communications network.

9. The method of claim 1, wherein the information provided includes a customer specific offer for at least one of hardware, software and training.

10. A system for optimizing a customer magnetic resonance (MR) system in a network of geographically dispersed customer MR systems, comprising:
    a computer geographically remote from the customer MR systems;
    an interface connected between the computer and a communication network, said interface configured to receive data relating to at least one of MR system usage or patient measurements from the customer MR systems;
    a non-transitory memory device accessible by the computer for storing the received data in a database;
    the computer configured by software stored in a non-transitory memory and executed by a processor of the computer to:
        perform data mining of the data stored in the database and analyze the mined data to perform a clustering of customer MR systems;
        learn at least one feature of a customer MR system selected based on the clustering; and
        provide information based on the at least one feature learned to another customer MR system based on the clustering, said providing including electronically programming the another customer MR system with the said at least one feature learned in order to optimize the another customer MR system;
    wherein the computer is configured to cluster a plurality of customer MR systems by:
        for every measurement obtained from a customer MR system of the plurality, finding two nearest neighbors, and obtaining a first distance for a first nearest neighbor and obtaining a second distance for a second nearest neighbor;

finding an average first distance with respect to an average second distance for all measurements of the customer MR system; and clustering the plurality of customer MR systems based on a position of each customer MR system for the average first distance and the average second distance.

11. The system of claim 10, wherein the feature learned includes at least one best-in-class protocol.

12. The system of claim 11, wherein the information provided includes a protocol derived from the at least one best-in-class protocol.

13. The system of claim 12, wherein the information provided further includes at least one measurement for at least one particular body region.

14. The system of claim 10, wherein the received data includes MR system sequence usage for at least one customer.

15. The system of claim 10, wherein clustering is performed using all measurements for at least one customer.

16. The system of claim 10, wherein the information provided includes at least one protocol learned from the customer MR system and provided to the another customer MR system.

17. The system of claim 16, wherein the at least one protocol learned is provided to the another customer MR system electronically via a communications network.

18. The system of claim 10, wherein the information provided includes a customer specific offer for at least one of hardware, software and training.

* * * * *